United States Patent
Hicks, Jr.

(10) Patent No.: US 6,312,952 B1
(45) Date of Patent: Nov. 6, 2001

(54) IN VITRO CELL CULTURE DEVICE INCLUDING CARTILAGE AND METHODS OF USING THE SAME

(75) Inventor: Wesley L. Hicks, Jr., Angola, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/579,805

(22) Filed: May 26, 2000

Related U.S. Application Data (60) Provisional application No. 60/136,610, filed on May 27, 1999.

(51) Int. Cl.$^7$ ................................. C12N 5/00; C12N 5/02
(52) U.S. Cl. ............................ 435/373; 435/325; 435/395; 435/402; 435/177
(58) Field of Search ..................... 435/325, 373, 435/395, 402, 177

(56) References Cited

U.S. PATENT DOCUMENTS

| | | | |
|---|---|---|---|
| 4,846,835 | * | 7/1989 | Grande . |
| 5,326,357 | * | 7/1994 | Kandel . |
| 5,607,920 | * | 3/1997 | Kato et al. . |
| 5,736,372 | * | 4/1998 | Vacanti et al. ................... 435/180 |
| 5,759,190 | * | 6/1998 | Vibe-Hansen et al. ............. 606/151 |
| 5,769,899 | * | 6/1998 | Schwartz et al. .................. 623/18 |
| 5,786,217 | * | 7/1998 | Tubo et al. . |
| 5,928,945 | * | 7/1999 | Seliktar et al. . |
| 5,932,459 | * | 8/1999 | Sittinger et al. ................... 435/180 |
| 6,001,352 | * | 12/1999 | Boyan et al. . |

* cited by examiner

Primary Examiner—Christopher R. Tate
(74) Attorney, Agent, or Firm—Nixon Peabody LLP (57) ABSTRACT

The present invention relates to an in vitro cell culture device which includes a vessel comprising an inner surface, a layer of cartilage disposed on at least a portion of said inner surface, the layer of cartilage including a plurality of chondrocytes in an extracellular matrix, and a growth medium in the vessel, the layer of cartilage being bathed in the growth medium. Also disclosed is a composite cell culture prepared from the in vitro cell culture device, the composite cell culture includes a first layer including chondrocytes in an extracellular matrix, a second layer disposed on the first layer and including type I collagen, and a third layer disposed on the second layer and including cells at least partially covering the second layer. Further aspects of the present invention relate to methods of preparing an in vitro composite cell culture, methods of screening putative therapeutic agents for activity in promoting re-epithelialization of cartilaginous tissues, and methods of screening putative therapeutic agents for activity in inhibiting growth factors or proteinases.

11 Claims, 8 Drawing Sheets

IN VITRO CELL CULTURE DEVICE INCLUDING CARTILAGE AND METHODS OF USING THE SAME

The present invention claims the priority benefit of U.S. Provisional Patent Application Ser. No. 60/136,610, filed May 27, 1999, which is hereby incorporated by reference.

The present invention was funded by the National Institutes of Health, Grant No. K08-CA01659. The U.S. Government may have certain rights in the present invention.

FIELD OF THE INVENTION

The present invention relates to an in vitro cell culture including cartilage, as well as various uses thereof, including screening for compounds which can modify cell/cell or cartilage/cell interactions.

BACKGROUND OF THE INVENTION

Restoration of epithelial tissue after tissue injury is a complex process, which includes several critical events, including deposition of extracellular matrix ("ECM"), tissue remodeling, and angiogenesis. These events are coordinated with epithelial cell migration and proliferation to restore the epithelial and/or mucosal barrier (i.e., in epithelial tissues such as tracheal epithelium which secrete mucous). The coordination of these events is believed to involve the interaction between different classes of cells as well as between cells and their extracellular matrix.

Failure of re-epithelialization after injury has been observed in the cornea (Fini et al., "Expression of Collagenolytic/Gelatinolytic Metalloproteinases by Normal Cornea," *Invest. Opthalmol. Vis. Sci.* 31:1779–1788 (1990)) and in chronic wounds (Stacey et al., "Tissue and Urokinase Plasminogen Activators in the Environs of Venous and Ischemic Leg Ulcers," *Br. J. Surg.* 80:595–599 (1993); Wysocki et al., "Wound Fluid from Chronic Leg Ulcers Contains Elevated Levels of Metalloproteinases MMP-2 and MMP-9," *J. Invest. Dermatol.* 101:64–68 (1993); Madlener et al., "Matrix Metalloproteinases (MMPs) and their Physiological Inhibitors (THAPs) are Differentially Expressed During Excisional Skin Wound Repair," *Exp. Cell Res.* 242:201–210 (1998); Di Colandrea et al., "Epidermal Expression of Collagenase Delays Wound-healing in Transgenic Mice," *J. Invest. Dermatol.* 11:1029–1033 (1998)). Proteinases that destroy the basement membrane over which epithelial cells migrate have been implicated as mediators in impaired capacity to re-epithelialize.

Tissue remodeling during wound healing is critical for repair as cellular migration over an appropriate ECM requires controlled and tightly regulated proteolytic degradation of the ECM, with consequent activation or release of matrix-bound growth factors (Clark, "Basics of Cutaneous Wound Repair," *J. Dermatol. Surg. Oncol.* 19:693–706 (1993); Salo et al., "Expression of Matrix Metalloproteinase-2 and -9 During Early Human Wound Healing," *Lab. Invest.* 70:176–182 (1994); Vaalamo et al., "Patterns of Matrix Metalloproteinase and TIMP-1 Expression in Chronic and Normally Healing Human Cutaneous Wounds," *Br. J. Dermatol.* 135:5259–59(1996); Moses et al., "Temporal Study of the Activity of Matrix Metalloproteinases and Their Endogenous Inhibitors During Wound Healing," *J. Cell. Biochem.* 60:379–386 (1996); Martin "Wound Healing—Aiming for Perfect Skin Regeneration," *Science* 276:75–81 (1997); Arumagam et al., "Temporal Activity of Plasminogen Activators and Matrix Metalloproteinases During Cutaneous Wound Repair," *Surgery* 125:5887–593 (1999)).

As with the above-described tissues, re-epithelialization of injured tracheal tissues is often incomplete. The ability of respiratory epithelial cells ("RECs") to migrate and proliferate and restore denuded areas of the large conducting airway after injury is poor. Post-trauma restoration is pathologically manifested by the exuberant proliferation of granulation tissue and replacement of the normal respiratory epithelium with fibroblasts (Clark, "The Commonality of Cutaneous Wound Repair and Lung Injury," *Chest.* 99(Suppl.):57S–60S (1991); Grillo, "Tracheal Replacement,"*Ann. Thorac. Surg.* 49:864–865 (1990)). This often leads to scar formation, airway stenosis, and eventual physiologic compromise of the host respiratory tract.

There is currently no effective way to study events of re-epithelialization after injury, particularly with respect to the intraluminal events surrounding tracheal repair. Present approaches to tracheal repair include resection and reanastomosing the injured airway, replacement of the damaged portion by synthetic material, and use of autologous tissue for reconstruction of the tracheal defect (Letang et al., "Experimental Reconstruction of the Canine Trachea with a Free Revascularized Small Bowel Graft," *Ann. Thorac. Surg.* 49:955–958 (1990); Mulliken et al., Abstract, "The Limits of Tracheal Resection with Primary Anastomosis: Further Anatomical Studies in Man,"*J. Thorac. Cardiovasc. Surg.* 55:418 (1968); Neville et al., "Prosthetic Reconstruction of the Trachea and Carina," *J. Thorac. Cardiovasc. Surg.* 72:525–536 (1976)). Recently, tissue engineering approaches have been taken, including forming an in vivo tracheal cartilaginous scaffolding by injecting dissociated chondrocytes into a preformed synthetic construct (Hirano et al., "Hydroxylapatite for Laryngotracheal Framework Construction. *Ann. Otol. Rhinol. Laryngol.* 98:713–717 (1989); Okumura et al., "Experimental Study of a New Tracheal Prosthesis Made from Collagen Grafted Mesh," *Trans. Am. Soc. Artif. Organs.* 37:M317–M319 (1991); Langer et al., "Tissue Engineering," *Science* 260:920–926 (1993)). Such devices were of limited success owing to lack of reepithelialization. In the case of synthetic replacement, migration of the prosthesis can occur and may result in chronic ulceration, and even fatal hemorrhage (Grillo, "Tracheal Replacement", *Ann. Thorac. Surg.* 49:864–865 (1990)).

A frequent problem seen in tracheal repair with synthetic or autologous materials is the failure of luminal surface reepithelialization. Failure of reepithelialization to reestablish luminal integrity is an important reason why no acceptable surgical procedure exists for the repair of extended segments of trachea compromised by inhalation injury, congenital anomalies, or neoplastic disease.

Why the rate of reepithelialization in the large conducting airway is different from that seen within other epithelial-lined or -covered surfaces is unclear. The phenomenon of "slowed" reepithelialization is seen after both ablative surgical reconstruction and denudation injury, where the epithelium and basement membrane are removed with an intact cartilaginous superstructure (e.g., inhalation injury).

One of the difficulties in understanding the relationship between epithelium and its underlying substructure (cartilage and submucosa) is the inaccessibility of the tissue for direct observation. It would be desirable, therefore, to provide an in vitro cell culture which includes a developed substructure or cartilaginous layer which can be used to study epithelial cell development.

The present invention is directed to overcoming these and other deficiencies in the art.

SUMMARY OF THE INVENTION

One aspect of the present invention relates to an in vitro cell culture device which includes a vessel including an inner surface, a layer of cartilage disposed on at least a portion of the inner surface, the layer of cartilage including a plurality of chondrocytes in an extracellular matrix, and a growth medium in the vessel, the layer of cartilage being bathed in the growth medium.

A further aspect of the present invention relates to a composite cell culture which includes a first layer including chondrocytes in an extracellular matrix, a second layer disposed on the first layer and including type I collagen, and a third layer disposed on the second layer and including cells at least partially covering the second layer.

Another aspect relates to a method for preparing an in vitro composite cell culture. This method is carried out by providing an in vitro cartilage layer that includes chondrocytes in an extracellular matrix, disposing a type I collagen layer on the cartilage layer, and contacting the type I collage layer with epithelial cells under conditions effective for the epithelial cells to multiply and at least partially cover the layer of type I collagen.

Still another aspect of the present invention relates to a method of screening putative therapeutic agents for activity in promoting re-epithelialization of cartilaginous tissues. According to one approach, the method is carried out by introducing a putative therapeutic agent into a composite cell culture of the present invention and then assessing epithelial cell growth on the composite cell culture, wherein increased surface area coverage of a plurality of distinct plaques of epithelial cells indicates that the putative therapeutic agent has activity in promoting reepithelialization of cartilaginous tissues. Alternatively, this method is carried out by providing an in vitro cell culture device of the present invention, introducing a layer of type I collagen onto the layer of cartilage, introducing epithelial cells onto the layer of type I collagen to form a composite cell culture, introducing a putative therapeutic agent into the composite cell culture, and assessing epithelial cell growth on the composite cell culture, wherein growth and migration of epithelial cells beyond distinct plaques thereof indicates that the putative therapeutic agent has activity in promoting re-epithelialization of cartilaginous tissues.

Yet another aspect of the present invention related to a method of screening putative therapeutic agents for activity in inhibiting a growth factor or proteinase which prevents re-epithelialization of cartilaginous tissues. According to one approach, this method is carried out by introducing a putative therapeutic agent into a composite cell culture of the present invention and assessing epithelial cell growth on the composite cell culture, wherein increased surface area coverage of a plurality of distinct plaques of epithelial cells indicates that the putative therapeutic agent has activity in inhibiting a growth factor or proteinase which prevents re-epithelialization. Alternatively, this method is carried out by providing an in vitro cell culture device of the present invention, introducing a layer of type I collagen onto the layer of cartilage, introducing epithelial cells onto the layer of type I collagen to form a composite cell culture, introducing a putative therapeutic agent into the composite cell culture, and assessing epithelial cell growth on the composite cell culture, wherein growth and migration of epithelial cells beyond distinct plaques thereof indicates that the putative therapeutic agent has activity in inhibiting a growth factor or proteinase which prevents re-epithelialization.

The in vitro cell culture device of the present invention enables the growth of cells on an in vitro cartilage substructure, which enables the study of cell-cell interactions between chondrocytes and other cell types introduced onto the cell culture device, as well as cell-matrix interactions between cartilage and other cell types introduced onto the cell culture device. When collagen inserts are placed onto the cell culture device and isolated cells or tissues are introduced onto the collagen inserts, the resulting composite cell culture can similarly be used. In addition, the in vitro cell culture device and composite cell culture can be used to screen various therapeutic agents for their ability to modify such cell-cell or cell-matrix interactions, both on a cellular level as well as on a molecular level. The in vitro cell culture device and composite cell culture will facilitate the development of systems in which graft tissues can be raised in vitro for subsequent grafting onto a patient, preferably using the patient's own cells so as to avoid any undesirable immune reactions.

BRIEF DESCRIPTION OF THE DRAWINGS

FIGS. 2 A–C are enlarged images showing bovine chondrocytes in culture for 28 days after isolation. FIG. 2A shows hematoxylin-eosin staining at 165×; FIG. 2B shows electron microscopy at 300×; and FIG. 3C shows type II collagen staining at 83×.

FIGS. 3A–D are enlarged images by scanning electron micrograph of day 14 control and composite cell cultures. FIGS. 3A and 3B illustrate the difference between confluent epithelium on the control cell culture (3A, magnification 32×) and distinct patches of respiratory epithelium on the composite cell culture (3B, magnification 100×). FIGS. 3C (magnification 32×) and 3D (magnification 100×) illustrate respiratory epithelium on composite cell cultures, with arrows indicating nonconfluent epithelium.

FIGS. 5A–B are images illustrating the results of gelatin zymography for matrix metalloproteinase ("MMP") activity performed on media conditioned by respiratory epithelial cells and chondrocytes. Pre-stained molecular weight markers and purified MMP-2 and -9 standards were included. Serum-free media ("SFM")and REC-conditioned media were mixed with sample buffer and run undiluted. Chondrocyte-conditioned media ("CCM") was diluted 5-fold in sample buffer. FIG. 5A represents a Coomassie blue-stained gelatin zymogram run in the absence of EDTA. Clear areas represent zones of substrate lysis. FIG. 5B represents a zymogram incubated with the divalent cation chelator EDTA. MW, molecular weight marker proteins with individual bands indicated; lane 1, MMP standards (5 ng/nd); lane 2, MMP standards (1 ng/ml); lane 3, SFM; lane 4, REC-conditioned medium; lane 5, day 3 serum-containing CCM; lane 6, day 3 serum-free CCM. Upper arrow indicates MMP-9 (92 kDa gelatinase); lower arrow indicates MMP-2 (72 kDa gelatinase).

FIG. 6 is a graph illustrating the effect of CCM in reducing proliferation of REC. Viability of the control and treated cultures was equivalent (97.7±1.0% for control; 94.1±2.9o/o for CCM). Values represent average cell number ±SEM from triplicate cultures in a representative experiment; *indicates a significant difference (P<0.01) between control and treated cultures.

FIG. 7A shows medium collected on day 3 of culture and FIG. 7B shows medium collected on day 7. Lane 2, MMP-2/MMP-9 standards (10 ng/ml). Upper arrow indicates 92 kDa gelatinase (MMP-9) and lower arrow indicates 72 kDa gelatinase (MMP-2). Media were pre-incubated with p-aminophenylmercuric acetate to activate latent enzyme activity prior to analysis. Lane 3, SFM; lane 4, day 3 REC conditioned medium; lane 5, control SFM; lane 6, control+ negative drug; lane 7, CCM; lane 8, CCM+GM6001; lane 9, CCM+negative drug.

DETAILED DESCRIPTION OF THE INVENTION

One aspect of the present invention relates to an in vitro cell culture device which can be used to grow cells and study cell-cartilage or cell-cell interactions, to measure the efficacy of potential therapeutic agents on chondrocytes or other cell types, and to grow tissues with developed substructure for subsequent implantation.

The in vitro cell culture device includes a vessel having an inner surface, a layer of cartilage disposed on at least a portion of the inner surface, where the layer of cartilage includes a plurality of chondrocytes in an extracellular matrix, and an amount of growth medium in the vessel sufficient to bathe the layer of cartilage.

The vessel can be any suitable walled structure which enables development of an in vitro cell culture device or three-dimensional composite cell culture of the present invention. The vessel is preferably formed of glass or a high-grade thermoplastic material which is suitable for such uses.

Figure 1:
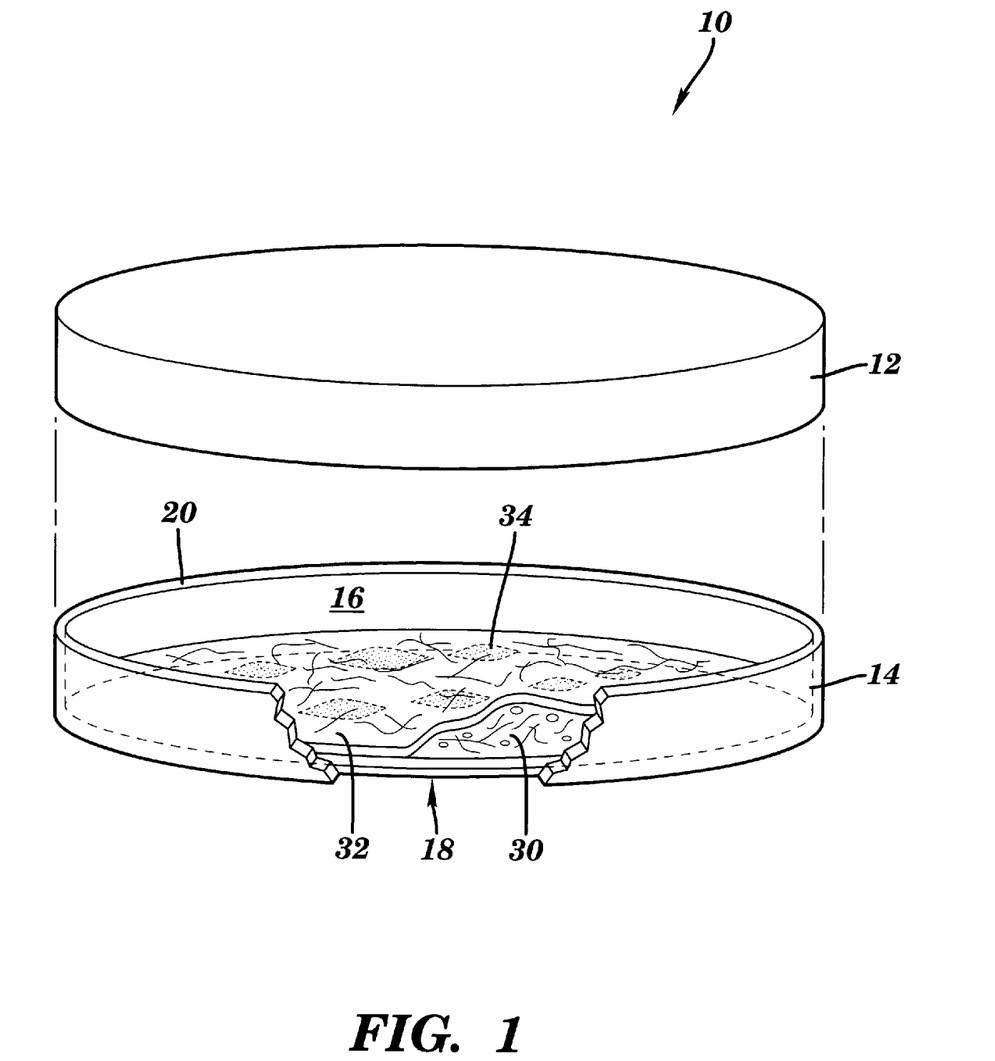
FIG. 1 is a partially exploded view of an in vitro cell culture device of the present invention which has been used to prepare a composite cell culture of the present invention.

According to one embodiment, illustrated in FIG. 1, the vessel of the in vitro cell culture device 10 is in the form of a petri dish having upper 12 and lower 14 members. The lower member 14 has an inner surface 16 defined by bottom 18 and integral sidewall 20. The layer of cartilage 30 is present adjacent to the bottom 18. When used to grow a composite cell culture of the present invention, as shown in FIG. 1, a layer of collagen (e.g., type I collagen) 32 is disposed on the layer of cartilage 30, and a partial layer of cells 34 is deposited on the layer of collagen 32. As shown, the partial layer of cells 34 develops to form discrete patches or plaques of cells rather than a confluent layer of such cells. By introducing a therapeutic agent capable of enabling cell proliferation and migration, the partial layer of cells 34 is then allowed to grow to confluence.

The chondrocytes used in the in vitro cell culture device of the present invention can be any suitable type of chondrocyte. Chondrocytes are cells found in various types of cartilage, e.g., articular (or hyaline) cartilage, elastic cartilage, and fibrocartilage. Specifically, chondrocytes are mesenchymal cells that have a characteristic phenotype based primarily on the type of extracellular matrix they produce. Precursor cells produce type I collagen, but when they become committed to the chondrocyte lineage, they synthesize type II collagen, which is a substantial portion of the extracellular matrix. In addition, committed chondrocytes produce proteoglycan aggregate, called aggrecan, which has glycosaminoglycans that are highly sulfated.

According to one embodiment of the present invention, the chondrocytes employed in an in vitro cell culture device are upper airway cartilage chondrocytes.

Suitable chondrocytes can be isolated from any suitable mammalian source organism, including, without limitation, human, orangutan, monkey, chimpanzee, dog, cat, rat, mouse, horse, cow, pig, etc.

Chondrocyte cells used for preparation of the in vitro cell culture device of the present invention can be isolated by any suitable method. Various starting materials and methods for chondrocyte isolation are known (see generally, Freshney, *Culture of Animal Cells: A Manual of Basic Techniques*, 2d ed., A. R. Liss Inc., New York, pp 137–168 (1987); Klagsburn, "Large Scale Preparation of Chondrocytes," *Methods Enzymol.* 58:560–564 (1979), which are hereby incorporated by reference) and are easily reproduced by those of skill in the art.

If the starting material is a tissue in which chondrocytes are essentially the only cell type present, e.g., articular cartilage, the cells can be obtained directly by conventional collagenase digestion and tissue culture methods. Alternatively, the cells can be isolated from other cell types present in the starting material. One known method for chondrocyte isolation includes differential adhesion to plastic tissue culture vessels. In a second method, antibodies that bind to chondrocyte cell surface markers can be coated on tissue culture plates and then used selectively to bind chondrocytes from a heterogeneous cell population. In a third method, fluorescence activated cell sorting (FACS) using chondrocyte-specific antibodies is used to isolate chondrocytes. In a fourth method, chondrocytes are isolated on the basis of their buoyant density, by centrifugation through a density gradient such as Ficoll.

It may be desirable in certain circumstance to utilize chondrocyte stem cells rather than differentiated chondrocytes. Examples of tissues from which stem cells for differentiation, or differentiated cells suitable for transdifferentiation, can be isolated include placenta, umbilical cord, bone marrow, skin, muscle, periosteum, or perichondrium. Cells can be isolated from these tissues by explant culture and/or enzymatic digestion of surrounding matrix using conventional methods.

Once the chondrocytes have been isolated, they are preferably plated onto collagen inserts at a suitable cell density (i.e., about 20 to about $40 \times 10^6$ cells per well) in a suitable growth medium. A number of suitable chondrocyte growth media are known in the art and modifications of known growth media can readily be made to optimize growth of such chondrocytes and their formation of an extracellular matrix. One suitable growth medium includes Dulbecco's modified Eagle's medium ("DMEM") containing 10% fetal bovine serum (FBS), 1% antibiotics and 50 mu g/ml ascorbic acid (Gibco, Grand Island, N.Y.). Other known culture media include, without limitation, RPMI 1640, Fisher's, Iscove's or Mccoy's, all of which are commercially available. Other additives may also be included in the chondrocyte growth medium, such as platelet-derived growth factor ("PDGF"), which has been shown to increase cartilage cell number without promoting further differentiation along the endochondral differentiation pathway (see U.S. Pat. No. 6,001,352 to Boyan et al., which is hereby incorporated by reference).

The collagen inserts preferably contain substantially pure type I collagen, i.e., at least 80% type I collagen, preferably at least 85% type I collagen, and more preferably, at least 90% type I collagen. The chondrocytes are maintained for about 21 to about 30 days or until the extracellular matrix is sufficiently developed. Suitable development of the extracellular matrix, denoting cartilage formation, is demonstrated by the following observations: opacity of culture, thickness of culture (i.e., between about 2–4 mm), and the firmness. This is achieved when the culture is brought to air interface.

Having established the development of the layer of chondrocytes in extracellular matrix within the vessel, the in vitro cell culture device can then be used to (i) study the relationship or interaction between chondrocytes and/or the extracellular matrix ("ECM") with other cells or tissues that can be introduced into the in vitro cell culture device; (ii) identify putative therapeutic agents which are capable of modifying cell-cell or cell-ECM interactions; or (iii) grow developed tissues along with substructure for subsequent implantation.

After development of the extracellular matrix, a second layer which includes collagen, preferably type I collagen, is applied over the layer of chondrocytes in the extracellular matrix (i.e., cartilage). The type I collagen preferably forms a substantial portion of the second layer. The type I collagen can readily be isolated and purified from a number of sources or it is otherwise commercially available, for example, from Vitrogen, Collagen Biomaterials (Palo Alto, Calif.). The type I collagen is preferably at least about 80% pure, more preferably at least about 85% pure, most preferably about 90% pure. It can be applied over the cartilage layer until a thickness of about 0.5–2 mm is achieved. Obviously, the volume of type I collagen which is needed to achieve such thickness will vary with the size of the vessel in which the culture resides.

On top of the second layer containing collagen is applied a growth medium including a particular type of cell(s), whose growth in the in vitro cell culture device is desired. Once introduced onto the second layer, a third layer is formed which includes the cells at least partially covering the second layer.

Suitable cell types which can be used to develop a three-dimensional, composite cell culture include epithelial cells, fibroblasts, endothelial cells, epidermal cells, muscle cells, or combinations thereof. The cells can be isolated from any tissue source of a suitable mammalian organism. The mammalian organism can be the same or different from the organism from which the chondrocytes were obtained. The cells can be added to the layer of collagen at rate of about $1.0–10.0 \times 10^5$ cells per $cm^2$, preferably about $1.0–5.0 \times 10^5$ cells per $cm^2$, more preferably about $1.5–3.5 \times 10^5$ cells per $cm^2$. Suitable growth media include those described above, or otherwise known in the art for growth of particular cell types.

Once the cells have been introduced onto the collagen layer in the in vitro cell culture device, the cells should be allowed to grow until the cell layer has grown to confluence or until the growth of such cells otherwise has sufficiently mimicked in vivo growth of such cells. Once the growth of cells has been established, whether to confluence or not, the in vitro cell culture device contains a composite cell culture of the present invention. The composite cell culture represents a three-dimensional tissue model that is particularly well adapted for studying cell-cell or cell-substructure interactions.

A further aspect of the present invention relates to a method of preparing an in vitro composite cell culture. This method is carried by providing an in vitro cartilage layer including chondrocytes in an extracellular matrix, disposing a collagen (e.g., type I collagen) layer on the cartilage layer, and then contacting the collage layer with cells under conditions effective for the cells to multiply and at least partially cover the layer of collagen.

As described above, the method can also include providing a collagen (e.g., type I collagen) substrate on which the in vitro cartilage layer can be raised. Providing the in vitro cartilage layer can be carried out by first providing a chondrocyte single cell suspension and then culturing the chondrocytes under conditions effective to form an extracellular matrix, thereby forming cartilage in vitro. The culturing of chondrocytes, as noted above, is carried out by introducing the chondrocyte single cell suspension onto the collagen substrate, preferably at a cell density of about $1–10 \times 10^6$ cells/$cm^2$.

The chondrocyte single cell suspension can be obtained according to any of the above-mentioned approaches for isolating chondrocytes. A preferred approach is carried out by providing articular cartilage which includes chondrocytes embedded in an extracellular matrix, and then treating the articular cartilage with collagenase II under conditions effective to digest the extracellular matrix and produce a chondrocyte single cell suspension.

According to one embodiment of the present invention, which is illustrated in FIG. 1, the growth of RECs in an in vitro cell culture device of the present invention mimics the reepithelialization of injured tracheal tissues. Chondrocytes are isolated from bovine articular cartilage and cells introduced onto the collagen layer are basal epithelial cells, secretory epithelial cells, or a combination thereof, isolated from upper respiratory tract epithelial tissues (i.e., bronchus, nasal polyps, or turbinates). The upper respiratory tract epithelium can be dissociated using any suitable method, for example, as described in Hicks et al., Abstract, "Rapid Isolation of Upper Respiratory Cells," *Mol. Biol. Cell.* 5(Suppl):118 a (1994), which is hereby incorporated by reference. The isolated epithelial cells are introduced onto the collagen layer in a suitable growth medium and at a rate indicated above. The ability of RECs to migrate and proliferate to restore denuded areas of the large conducting airway after injury is poor, often resulting in incomplete reepithelialization. This embodiment of the in vitro cell culture device mimics the in vivo pattern of reepithelialization, yielding discrete patches of the RECs rather than a confluent layer of RECs.

Without being bound by any particular theory, it is believed that communication between epithelial cells and underlying substructure (i.e., chondrocytes and/or extracellular matrix) is responsible for modulation of epithelial cell growth and differentiation through the release of growth factors and other proteins. Secreted agents which are believed to modify REC growth include matrix metalloproteinases ("MMPs") and transforming growth factors ("TGF").

Transforming growth factor-α ("TGF-α") is a member of the epidermal growth factor family and plays an important role in wound healing (Schultz et al., "Epithelial Wound Healing Enhanced by Transforming Growth Factor-α and Vaccinia Growth Factor," *Science* 235:350–352 (1987); Polk et al., "Increased Production of Transforming Growth Factor-α Following Acute Gastric Injury," *Gastroenterology* 102:1467–1474 (1992); and Madtes et al., "Expression of Transforming Growth Factor-α and Epidermal Growth Factor Receptor is Increased Following Bleomycin-Induced Lung Injury in Rats," *Am. J. Respir. Cell Mol. Biol.* 11: 540–551 (1994), which are hereby incorporated by reference). Transforming growth factor $β_1$ ("TGF-β") is a multifunctional polypeptide with differing cell-specific effects, including stimulation or inhibition of proliferation, and regulation of extracellular matrix production and remodeling (Massague et al., "The Transforming Growth Factors Family," *Ann. Rev. Cell. Biol.* 6:597–641 (1990); Raghow, Role of Transforming Growth Factors in Repair and Fibrosis," *Chest.* 99(Suppl.):61S–65S (1991); and Santala et al., "Regulation of Integrin-Type Cell Adhesion Receptors by Cytokines," *J. Biol. Chem.* 266:23505–23509 (1991), which are hereby incorporated by reference).

MMPs constitute a family of zinc-containing proteinases acting at neutral pH, that together are capable of degrading all components of the extracellular matrix. Substrates include collagen, gelatin, elastin, fibronectin, laminin, and proteoglycans, as well as nonmatrix substrates such as insulin-like growth factor-binding protein-3, tumor necrosis factor-α, fibroblast growth factor receptor 1, and angiogenic factors (Sehgal et al., "Novel Regulation of Type IV Collagenase (Matrix Metalloproteinase-9 and -2) Activities by Transforming Growth Factor-$β_1$ In Human Prostate Cancer Cell Lines," *Mol. Biol. Cell.* 10:407–416 (1999), which is hereby incorporated by reference). They are secreted in latent form as propeptides requiring activation for proteolytic activity, and are inhibited by endogenous tissue inhibitors of metalloproteinases (Nagase et al., "Involvement of Tissue Inhibitors of Metalloproteinases (TEMPs) During Matrix Metalloproteinase Activation," *Adv. Exp. Med. Biol.* 389:23–31 (1996); Parsons et al., "Matrix Metalloproteinases," *Br. J. Surg.* 84:160–166 (1997); Shapiro, "Matrix Metalloproteinase Degradation of Extracellular Matrix: Biological Consequences," *Curr. Opin. Cell. Biol.* 10:602–608 (1999); Toi et al., "Metalloproteinases and Tissue Inhibitors of Metalloproteinases," *Breast Cancer Res. Treat.* 52:113–124 (1998), which are hereby incorporated by reference). Marker protein synthesis is transcriptionally enhanced by several growth factors including epidermal growth factor, basic fibroblast growth factor, platelet-derived growth factor, and nerve growth factor, and by inflammatory cytokines such as tumor necrosis factorα and interleukin-1. Inhibitory agents include transforming growth factor-P, retinoic acid, gamma interferon, glucocorticoids, progesterone, and estrogen (Nagase et al., "Involvement of Tissue Inhibitors of Metalloproteinases (TEMPs) During Matrix Metalloproteinase Activation," *Adv. Exp. Med. Biol.* 389:23–31 (1996); Sehgal et al., "Novel Regulation of Type IV Collagenase (Matrix Metalloproteinase-9 and -2) Activities by Transforming Growth Factor-$μ1$ in Human Prostate Cancer Cell Lines," *Mol. Biol. Cell.* 10:407–416 (1999), which are hereby incorporated by reference). Inappropriate or excessive production of MMPs may contribute to tissue destruction in arthritis, multiple sclerosis, periodontal disease, cardiovascular disease, tumor progression, and chronic pulmonary obstructive disease (Shapiro, "Matrix Metalloproteinase Degradation of Extracellular Matrix: Biological Consequences," *Curr. Opin. Cell. Biol.* 10:602–608 (1999), which is hereby incorporated by reference).

In particular, MMP-2 and -9 (type IV collagenases/gelatinases proenzymes are produced by chondrocytes and play a major role in cartilage remodeling and loss of extracellular matrix in osteoarthritis (Lefebvre et al., "Production of Gelatin-degrading Matrix Metalloproteinases ('Type IV Collagenases') and Inhibitors by Articular Chondrocytes During their Dedifferentiation by Serial Subcultures and Under Stimulation by Interleukin-1 and Tumor Necrosis Factor α," *Biochem. Biophys. Acta.* 1094:8–18 (1991), which is hereby incorporated by reference).

Since one embodiment of the in vitro composite cell culture of the present invention mimics the in vivo cartilage/epithelial cell interactions following tracheal injury, this particular composite cell culture can be used to screen for putative therapeutic agents which can promote proper reepithelialization of cartilaginous tissues. Generally, this aspect of the present invention is carried out by introducing a putative therapeutic agent into a composite cell culture or in vitro cell culture device of the present invention and assessing cell (e.g., epithelial cell) growth on the composite cell culture.

This aspect of the present invention can be used to screen putative therapeutic agent(s) for their ability to inhibit normal in vivo collagen/epithelial cell interaction or, more specifically, the effect of matrix metalloproteinases or growth factors on such epithelial cells. Putative therapeutic agent(s) can be introduced, either alone or in combination, onto the in vitro cell culture device either before the addition of the epithelial cells, at the same time the epithelial cells are introduced (i.e., in the same medium), or thereafter. The putative therapeutic agent(s) can then be screened for their ability to disrupt the undesirable inhibition of epithelial cell growth and proliferation. Statistically significant cell growth or proliferation of epithelial cells while in the presence of a putative therapeutic agent will indicate an ability of the therapeutic agent to enable re-epithelialization of cartilage substructure following tracheal injury. Effectiveness of the putative therapeutic agent can be detected, for example, by measuring increased surface area coverage of the plurality of distinct plaques. In some cases, the epithelial cells can even grow to confluence.

According to one embodiment, the screening of putative therapeutic agents for activity in promoting re-epithelialization of cartilaginous tissues is carried out by introducing a putative therapeutic agent into a composite cell culture of the present invention and then assessing epithelial cell growth on the composite cell culture, wherein increased surface area coverage of the plurality of distinct plaques indicates that the putative therapeutic agent has activity in promoting re-epithelialization of cartilaginous tissues.

According to another embodiment, the screening of putative therapeutic agents for activity in promoting re-epithelialization of cartilaginous tissues is carried out by providing an in vitro cell culture device of the present invention, introducing a layer of type I collagen onto the layer of cartilage, introducing epithelial cells onto the layer of type I collagen, thereby forming a composite cell culture, introducing a putative therapeutic agent into the composite cell culture, and then assessing epithelial cell growth on the composite cell culture, wherein growth and migration of epithelial cells beyond distinct plaques thereof indicates that the putative therapeutic agent has activity in promoting re-epithelialization of cartilaginous tissues.

According to a further embodiment, the screening of putative therapeutic agents for activity in inhibiting a growth factor or proteinase which prevents re-epithelialization of cartilaginous tissues is carried out by introducing a putative therapeutic agent into a composite cell culture of the present invention and then assessing epithelial cell growth on the composite cell culture, wherein increased surface area coverage of the plurality of distinct plaques indicates that the putative therapeutic agent has activity in inhibiting a growth factor or proteinase which prevents re-epithelialization.

According to a yet another embodiment, the screening of putative therapeutic agents for activity in inhibiting a growth factor or proteinase which prevents re-epithelialization of cartilaginous tissues is carried out by providing an in vitro cell culture device of the present invention, introducing a layer of type I collagen onto the layer of cartilage, introducing epithelial cells onto the layer of type I collagen, thereby forming a composite cell culture, introducing a putative therapeutic agent into the composite cell culture, and then assessing epithelial cell growth on the composite cell culture, wherein growth and migration of epithelial cells beyond distinct plaques thereof indicates that the putative therapeutic agent has activity in inhibiting a growth factor or proteinase which prevents re-epithelialization.

Following identification of suitable therapeutic agents which will allow for in vitro growth of confluent cell layers in a composite cell culture of the present invention, it is possible to prepare in vitro graftable tissue specimens that contain layers of cells over a substructural layer of cartilage. Such graftable tissue specimens can then be introduced into a patient using procedures known in the art.

EXAMPLES

The following examples are provided to illustrate embodiments of the present invention, but they are by no means intended to limit its scope.

Example 1

Isolation and Culture of Chondrocytes

Chondrocytes were harvested from bovine articulator cartilage under clean conditions, minced finely, and digested for 12 to 16 hours at 37° C. in phosphate buffered saline containing antibiotics, collagenase II (Worthington, Freehold, N.J.), and DNAse I (Sigma-Aldrich Corporation, St Louis, Mo.) as described by Klagsbum, "Large Scale Preparation of Chondrocytes," *Methods Enzymol.* 58:560–564 (1979), which is hereby incorporated by reference. Cell viability was determined by trypan blue staining, and cell type was confirmed by staining with hematoxylin-eosin and antibody to extracellular type II collagen. Chondrocytes were plated on collagen inserts (Co Eagle medium star Transwell; VWR, Rochester, N.Y.) at 20 to $40 \times 10^6$ cells per well in Dulbecco DMEM/F12 (Gibco, Grand Island, N.Y.) modified with antibiotics, 10% fetal calf serum, and 50-$\mu$g/mL ascorbic acid.

Figure 2A:
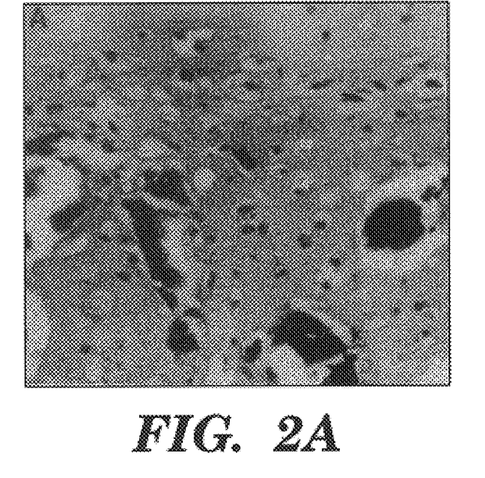
Figure 2B:
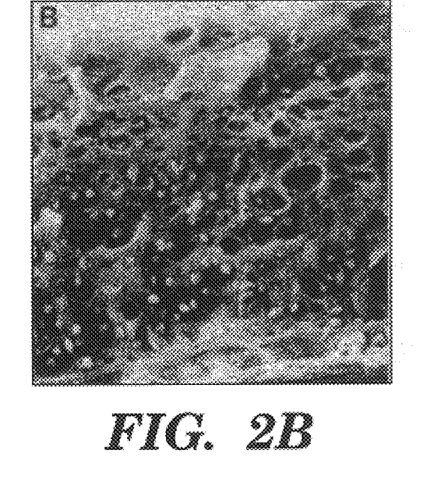
Figure 2C:
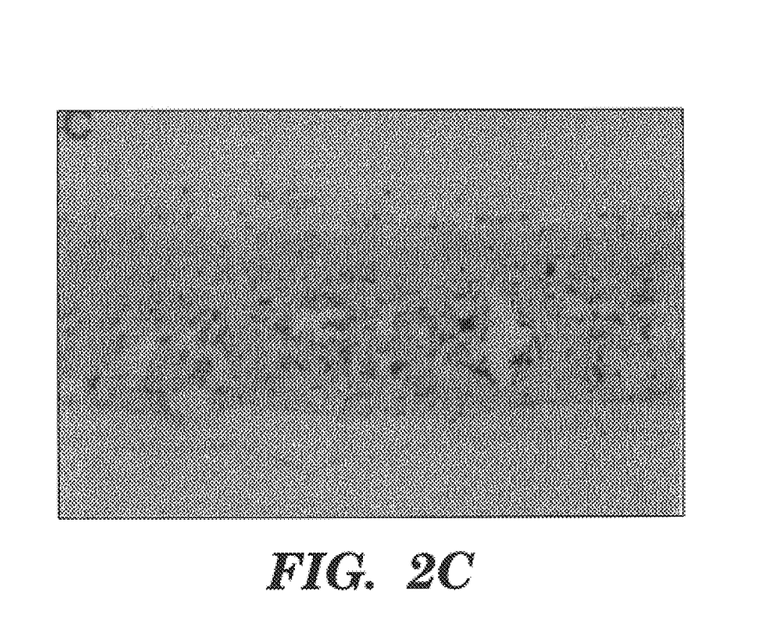

As shown in FIGS. 2A–B, bovine chondrocytes established in primary culture were morphologically similar to in vivo bovine cartilage. Cartilage cultured for less than 2 months did not always form lacunae, but always produced an abundant extracellular matrix of type II collagen (FIG. 2C.).

Example 2

Isolation of Upper Respiratory Epithelial Cells

Human tissue specimens were obtained through Manhattan Eye, Ear, Nose and Throat Hospital, New York, N.Y., under a human institutional review board approved protocol. Samples were healthy tissues from surgical procedures performed on adults. Specimens were removed aseptically, rinsed in isotonic sodium chloride solution to remove debris, and shipped at 4° C. within 24 hours of procurement. Upon receipt of the tissue samples, upper respiratory tract epithelium from bronchus, nasal polyps, or turbinates was dissociated as described in Hicks et al., Abstract, "Rapid Isolation of Upper Respiratory Cells," *Mol. Biol. Cell.* 5(Suppl): 118 a (1994), which is hereby incorporated by reference.

Example 3

Construction of Respiratory Epithelial Cell Containing Composite Cell Culture and Control Culture After chondrocytes, cultured as described in Example 1, formed a layer of extracellular matrix, 0.5 mL of type I collagen (Vitrogen; Collagen Biomaterials, Palo Alto, Calif.) was added to wells, thereby forming the first two layers of the composite. After addition of the type I collagen, upper respiratory epithelial cells harvested according to Example 2 were added to type I collagen-coated chondrocytes at $2 \times 10^5$ cm$^2$, in DMEM/F-12, containing antibiotics, epidermal growth factor (10 ng/mL), hydrocortisone (1 $\mu$mol/L), insulin (5 $\mu$g/mL), L-isoproterenol (1 $\mu$mol/L), and 5% fetal calf serum. Cultures were aged for two weeks.

Upper respiratory epithelial cells harvested according to Example 2 were also added at the same density onto type I collagen-coated culture dishes (i.e., without a layer of chondrocytes in extracellular matrix), thereby forming control cultures. The control cultures were aged for two weeks like the composite cell cultures.

Figure 3A:
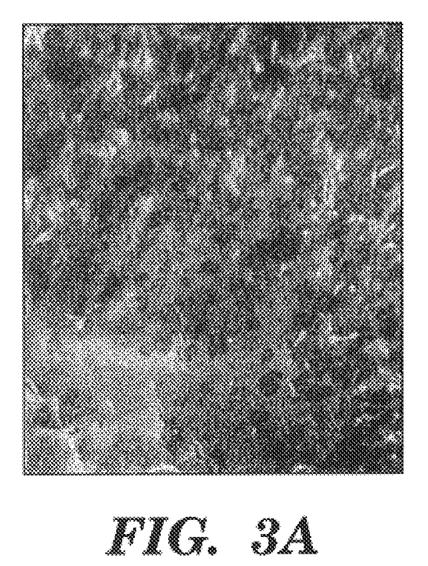
Figure 3B:
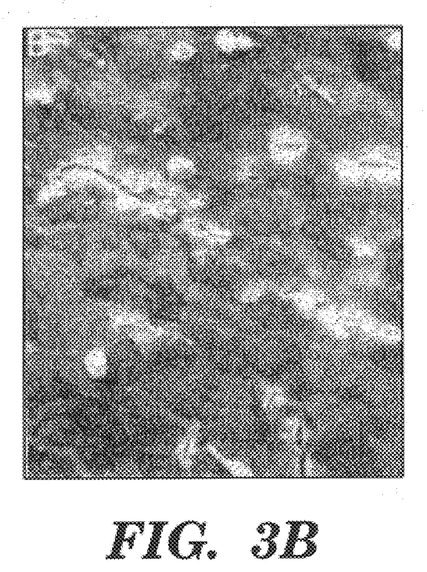
Figure 3C:
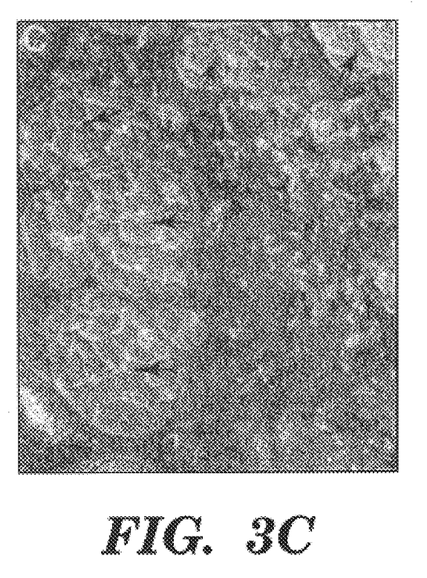
Figure 3D:
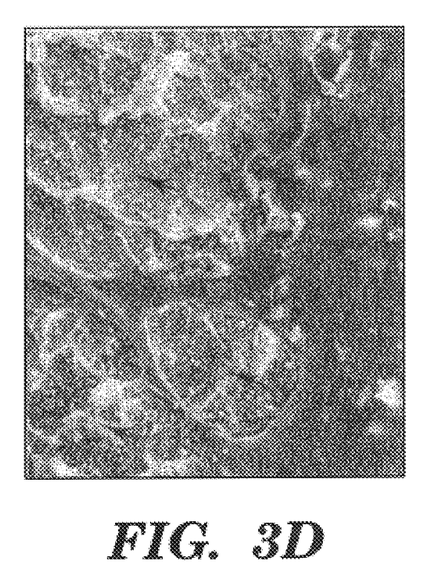

RECs grown on type I collagen formed a continuous sheet (FIGS. 3A–B). In contrast, RECs grown on composite cultures did not spread to confluence, but rather grew as discrete patches or plaques of epithelium (FIGS. 3C–D). The epithelial cell layer in both the composite cultures and on type I collagen was undifferentiated.

Example 4

Analysis of RECs and Chondrocytes for Growth Factor Expression

RECs from the aged composite cell cultures and control cultures were removed from the cultures by microscopic dissection and processed for RT-PCR (reverse transcriptase polymerase chain reaction. RECs were also processed for scanning electron microscopy (model 35 CF; JEOL, Japan) at 10 to 12 kV. The cartilage supernatant was taken for zymogram analysis.

Chondrocyte cultures aged twenty-eight days were formalin fixed and processed for immunoperoxidase histochemical analysis. Rabbit polyclonal antibody to type II collagen (DAKO, Carpinteria, Calif. was applied, washed, and followed by a biotinylated universal secondary antibody and streptavidin peroxidase (Immunon/Shandon-Lipshaw, Pittsburgh, Pa.).

Figure 4:
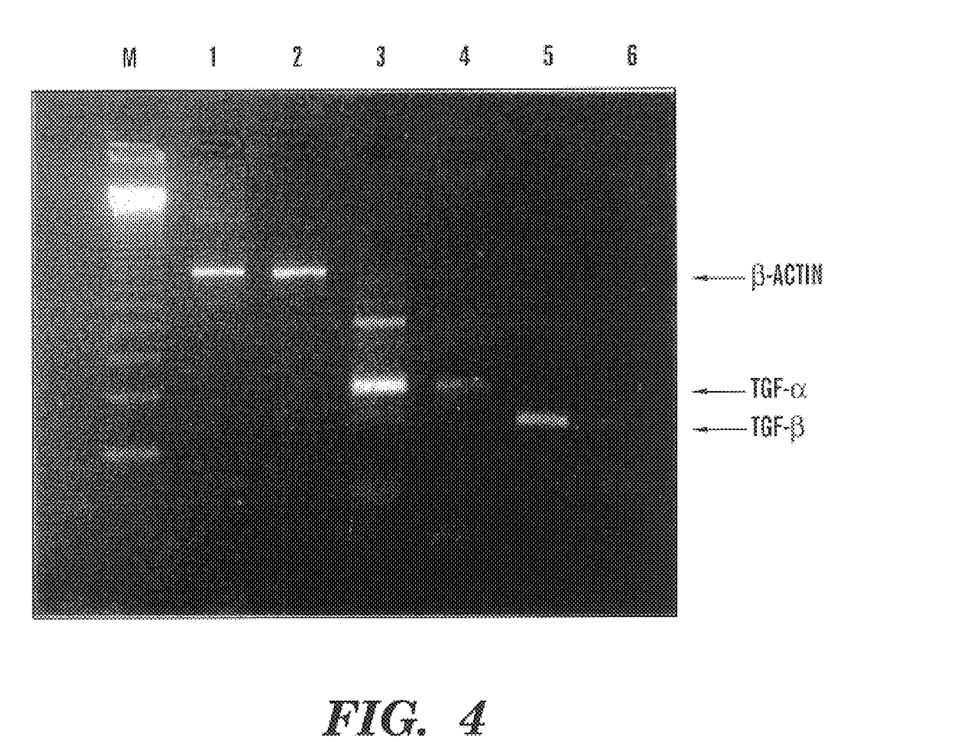
FIG. 4 is an image of a gel electrophoresis of RNA transcripts isolated from day 14 respiratory epithelial cells from control and composite cell cultures. M represents an RNA ladder; lane 1, β-actin from control culture; lane 2, β-actin from composite culture; lane 3, transforming growth factor-α ("TGF-α") from control culture; lane 4, TGF-α from composite culture; lane 5, transforming growth factor-β ("TGF-β") from control culture; lane 6, TGF-β from composite culture.

In REC from day 14 composite cultures, expression of both TGF-$\alpha$ and TGF-$\beta$ was reduced (FIG. 4, lane 4, TGF-$\alpha$; lane 6, TGF-$\beta$) as compared with REC on type I collagen (FIG. 4, lane 3, TGF-$\alpha$; lane 5, TGF-$\beta$). Relative expression of $\beta$-actin was equal (FIG. 4, lanes 1 and 2). Paraffin sections of REC grown on type I collagen and on composites were immunostained for TGF-$\alpha$ and TGF-$\beta$. Both growth factors were expressed in chondrocytes, and to a lesser extent, in epithelial cells.

Total cellular RNA was isolated from day 14 REC composite cell cultures, and REC control cultures using TriReagent (Molecular Research Center, Cincinnati, Ohio) as described by the manufacturer. Under a dissecting microscope, the REC layer was removed from cultures with a sterile, RNAse-free spatula into TriReagent. One to five micrograms of total RNA was reverse transcribed using murine Moloney leukemia virus reverse transcriptase (Kawasaki, *PCR Protocols: A Guide to Methods and Applications*, San Diego, Calif., Academic Press (1990), which is hereby incorporated by reference). Polymerase chain reaction amplification was performed using primer sets for human TGF-α, TGF-$β_1$, and β-actin (Clontech, Palo Alto, Calif.), following manufacturer's instructions. One-tenth volumes of polymerase chain reaction products were run on 2.5% or 3% agarose gels and visualized by ethidium bromide staining. The polymerase chain reaction products obtained were of expected sizes (human β-actin, 838 base pairs; human TGF-β, 161 bp; and human TGF-α, 297 bp).

Both TGF-α and TGF-β play crucial roles in new tissue formation and remodeling. TGF-α stimulates proliferation in cultured epithelial cells (Derynck, "Transforming Growth Factor-α: Structure and Biological Activities," *J. Cell Biochem.* 32:293–304 (1986), which is hereby incorporated by reference), fibroblasts (DeLarco et al., "Growth factors from murine sarcoma virus-transformed cells," *Proc. Natl. Acad. Sci. USA* 75:4001–4005 (1978), which is hereby incorporated by reference), and endothelial cells (Schreiber et al., "Transforming Growth Factor-α: A More Potent Angiogenic Mediator than Epidermal Growth Factor," *Science* 232:1250–1253 (1986), which is hereby incorporated by reference). It is chemotactic for epithelial cells in vitro (Barrandon et al., "Cell Migration Is Essential for Sustained Growth of Keratinocyte Colonies: The Roles of Transforming Growth Factor-α and Epidermal Growth Factor," *Cell* 50:1131–1137 (1987), which is hereby incorporated by reference) and enhances epithelial wound healing when applied topically (Schultz et al., "Epithelial Wound Healing Enhanced by Transforming Growth Factor-α and Vaccinia Growth Factor," *Science* 235:350–352 (1987), which is hereby incorporated by reference). TGF-β is mitogenic for cells of mesenchymal origin and plays a role in repair through its ability to modulate extracellular matrix formation and tissue remodeling.

When isolated human RECs were cultured on type I collagen, the cells spread to form a confluent layer as has been previously reported by other authors (Robinson et al., "Culture of Conducting Airway Epithelial Cells in Serum-Free Medium," *J. Tissue Cult. Method.* 13:95–102 (1991), which is hereby incorporated by reference). When plated onto composite cultures with a layer of type I collagen on top of cartilage, the cells did not spread efficiently but formed epithelial nests. Complete reepithelialization of the surface did not occur, even after 3 weeks.

Due to the physical differences between REC layers on the composite cell cultures and control cultures, TGF-α and TGF-β expression was examined. Both of these growth factors were reduced in epithelial cells from 14-day composite cultures when compared with the expression of these factors in REC cultured on type I collagen alone. This suggests that the cartilage modulates the behavior of epithelial cells. Without being bound by theory, it is believed that the observed diminished expression of TGF-α and TGF-β results from the secretion of soluble factors from the cartilage. TGF-α was expressed in cartilage, where it may have acted on the epithelium in a paracrine manner to decrease its expression.

Example 5

The Role of Matrix Metalloproteinases in Respiratory Epithelial Cell Attachment and Proliferation Chondrocytes were harvested from bovine or porcine articular cartilage according to the procedure set forth in Example 1. Cell viability and number were determined by Trypan blue staining and counting using a hemocytometer. Chondrocytes were plated on collagen inserts (Costar Transwell, VWR, Pittsburgh, Pa.) at 20–40×$10^6$ cells/well in DMEM/F12 containing antibiotics, 10% FBS, and 50 μg/ml ascorbic acid (prepared fresh and added every other day). After the chondrocytes had formed a layer of extracellular matrix (approximately 2 weeks), the medium was switched to serum free (DMEM/F 12 with antibiotics, 5 μg/ml insulin, 15 μg/ml bovine pituitary extract, 10 μg/ml epidermal growth factor, 5 μg/ml transferrin, 1 μM hydrocortisone, $10^{-8}$ M retinol, and ascorbic acid). Cultures were fed from the bottom every 3–4 days. Medium was collected from chondrocyte cultures on days 3, 5, 7, 10, and 14 after switching from 10% FBS-containing medium to SFM. The collected CCM was cleared by centrifugation to remove cell debris, pooled at every timepoint, and frozen at −20° C. until assayed. No protease inhibitors were added to collected medium.

Porcine tracheal tissue obtained at necropsy was cleaned of debris, rinsed thoroughly with PBS, and epithelium and submucosa removed and soaked overnight at 4° C. in MEM containing antibiotics/antimycotics. Dissociated respiratory epithelial cells were isolated using elastase digestion as described by Hicks et al. ("Rapid Isolation of Upper Respiratory Epithelial Cells," *Mol. Biol. Cells.*, 5(Suppl.): 118a (Abstract), (1995); Hicks et al., "Isolation and Characterization of Basal Cells from Human Upper Respiratory Epithelium," *Exp. Cell Res.* 237:357–363 (1997), which are hereby incorporated by reference) and plated on top of type I collagen-coated 35 mm petri dishes at 0.2×$10^6$ cells/$cm^2$ in serum free medium. In selected experiments, cells were cultured in Biocoat type I collagen-coated 24 well plates. Medium was collected for gelatin zymography as described above.

The proliferative effects of CCM on REC were assessed by addition of CCM diluted 1:1 with SFM. REC cultures grown on type I collagen were fed 0.1 ml CCM or control SFM daily, and media were changed completely every 3 days. At selected timepoints (days 5, 7, 10, and 14), cell cultures were harvested for determination of cell number by counting using a hemocytometer. For cells cultured on type I collagen 35 mm petri dishes, medium was removed and dishes rinsed twice with PBS. Type II collagenase at 2 mg/ml in PBS was added and the cultures incubated at 37° C. with gentle shaking for 45–60 minutes to allow digestion of the collagen substrate. Cells were collected and 10% FBS in DMEM added to stop digestion. Cells were washed once with PBS, and 2 × trypsin/EDTA solution added to further dissociate cells from the matrix and from one another. After incubation at 37° C. for 20 minutes, REC were again washed with PBS/10% FBS, then resuspended in PBS and an aliquot counted using Trypan blue dye exclusion to determine viability and cell number. For cells cultured in Biocoat 24 well plates, cells were removed by trypsinization, washed once in PBS/FBS and re-suspended in PBS for counting as described above. Results were similar between the two culture methods.

In selected experiments, GM6001, a broad-spectrum matrix metalloproteinase inhibitor, or its negative control peptide (both available from Calbiochem, San Diego, Calif.), were added to cells cultured in the presence or absence of CCM.

Seven and a half percent acrylamide gels were cast with 1 mg/ml gelatin as substrate. Latent proteases in media or standards were activated by incubating samples with 1 mM aminophenylmercuric acetate for 1 hour at 37° C. prior to electrophoresis.

CCM or SFM, obtained as described above, was mixed with 2× sample buffer (20 mM DTT, 4% SDS, 50 mM Tris, 20% glycine, 0.002% Bromophenol blue), loaded without prior heating, and electrophoresed under non-reducing conditions at 4° C .for approximately 4 hours under constant voltage. MMP-2 and MMP-9 standards (available from Chernicon, Temecula, Calif.) and kaleidoscope prestained molecular weight standards (available from Biorad, Hercules, Calif.) were included in every gel. After electrophoresis, gels were removed and washed twice in 2.5% Triton x-100 for 15 minutes each, then incubated in developing buffer (50 mM Tris-HCl, 0.2 M NaCl, 10 mM CaClhd 2, 0.02% (w/v) Brij 35, pH 7.5) overnight at 37° C., with moderate shaking. Some gels were incubated in developing buffer containing 20 mM EDTA (ethylenediamine tetraacetic acid) to chelate $Zn^2$ and inactivate the MMPs. Gels were rinsed twice with distilled water then stained for 1 hour in Coomassie blue stain, followed by destaining in water/methanol/acetic acid (6:3.5:0.5) until clear areas of enzyme activity were detected against a blue background. Estimates of amounts of MMPs present in CCM were made by comparison of known concentrations of MMP standards with dilutions of CCM and scanning the clear areas of substrate lysis on the gel by laser densitometry.

Experiments were performed a minimum of twice on independent tracheal REC preparations. Data were analyzed by ANOVA or t-test, as appropriate, with a level of statistical significance at $P<0.05$.

Figure 5A:
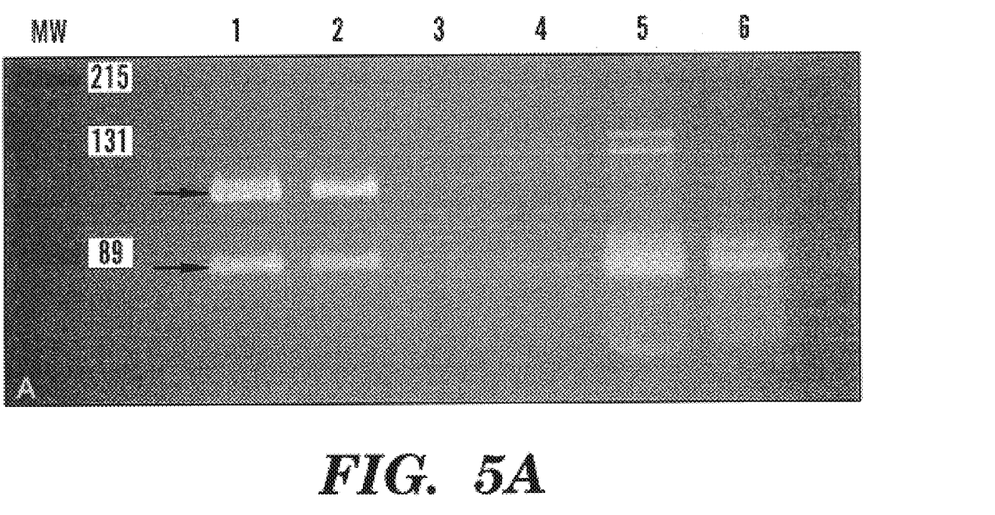
Figure 5B:
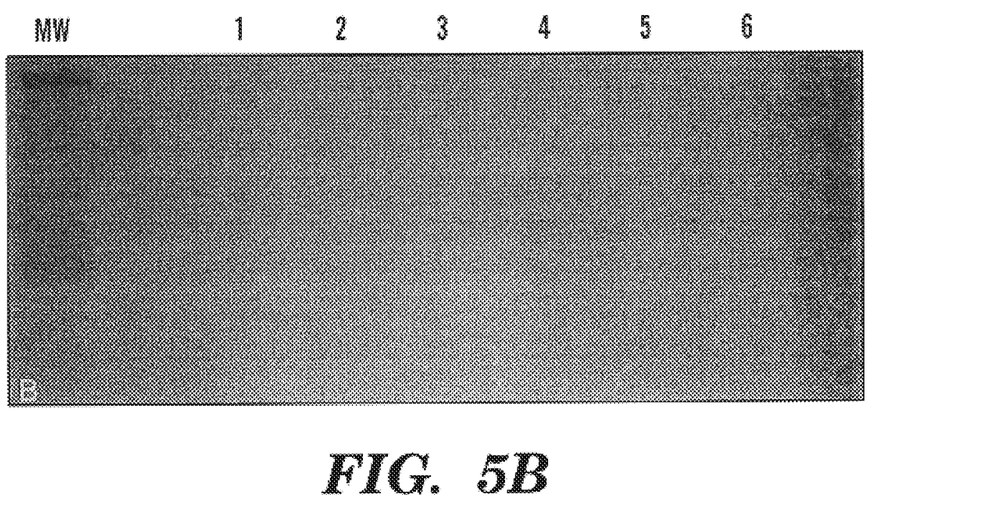

CCM from days 3, 5, 7, 10, and 14 was subjected to gelatin zymography on 7.5% SDS-PAGE gels. Several major bands of gelatinolytic activity were detected (FIG. 5A). Three distinct bands were observed at 105–125 kDa and two bands were detected at approximately 92 and 88 kDa. A major broad band was detected at 72 kDa with minor bands visible at 65–68 kDa. Based on comparisons with purified MMP-2 and -9 standards run in parallel with the samples, the areas of enzyme activity at 92 and 88 kDa corresponded to proMMP-9 and to active MMP-9. The bands of activity at 72 kDa corresponded to proMMP-2, and the lower molecular weight forms to activated forms of MMP-2. The higher molecular forms may represent additional gelatinases. When zymograms were developed in the presence of the chelator EDTA, enzyme activity was abolished and the clear areas of lysis disappeared, confirming the enzyme activity as belonging to matrix metalloproteinases (FIG. 5B).

Coincident with the secretion of matrix metalloproteinase-2 (MMP2, 72 kDa gelatinase) in cartilage, as determined by gel zymography, RECs that previously strongly expressed TGF-α and TGF-β had a decrease in the expression of both of these proteins in the composite cell culture.

SFM did not contain MMP activity (FIG. 5A, lane 3). Medium conditioned by respiratory epithelial cells cultured in SFM contained barely detectable MMP activity (FIG. 5A, lane 4). Conditioned medium from chondrocytes grown for 3 days in either 10% serum-containing medium or for 3 days after the switch to SFM exhibited considerable MMP activity as revealed by gelatin zymography (FIG. 5A, lanes 5 and 6, respectively).

Figure 6:
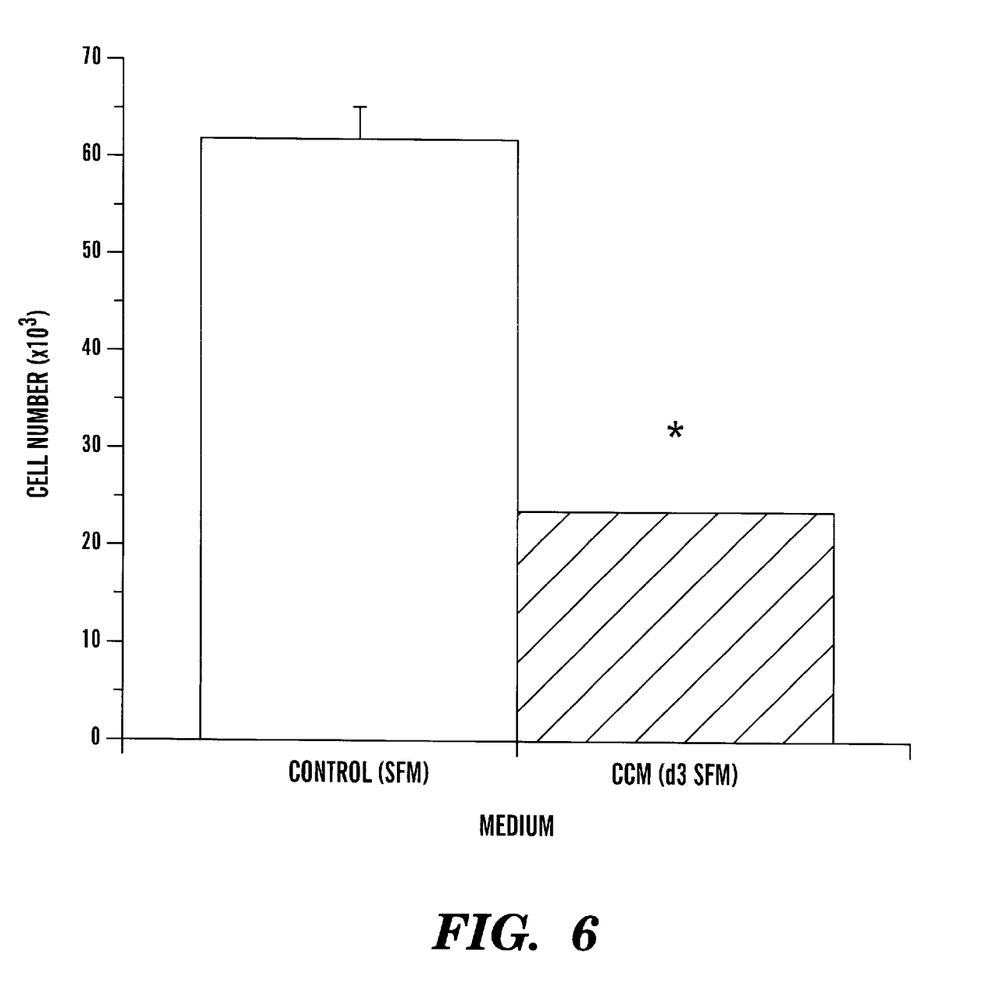

If matrix metalloproteinases were being secreted from chondrocytes, this may be a contributing factor in failure of epithelial cells to proliferate and spread to confluence over the covering type I collagen layer in the composite co-culture system (described in Example 3, supra). To ascertain this, serum-free CCM from days 3–14 was pooled and diluted in 1:1 with serum-free medium. This medium was fed to respiratory epithelial cells plated on type I collagen, and cell number was determined on day 7 of culture. Cell number was reduced by 61.3% in cultures that received CCM compared with controls that received SFM alone (FIG. 6), suggesting that MMPs secreted by chondrocytes may interfere with epithelial cell proliferation.

Figure 7A:
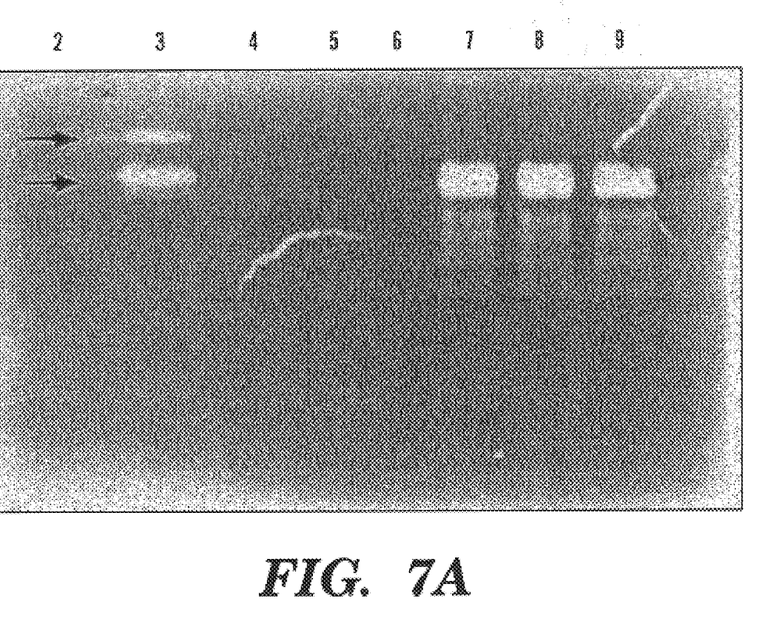
FIG. 7A–B are images illustrating the results of gel zymography for MMP activity performed on chondrocyte cultured medium with either an MMP inhibitor or its negative control.
Figure 7B:
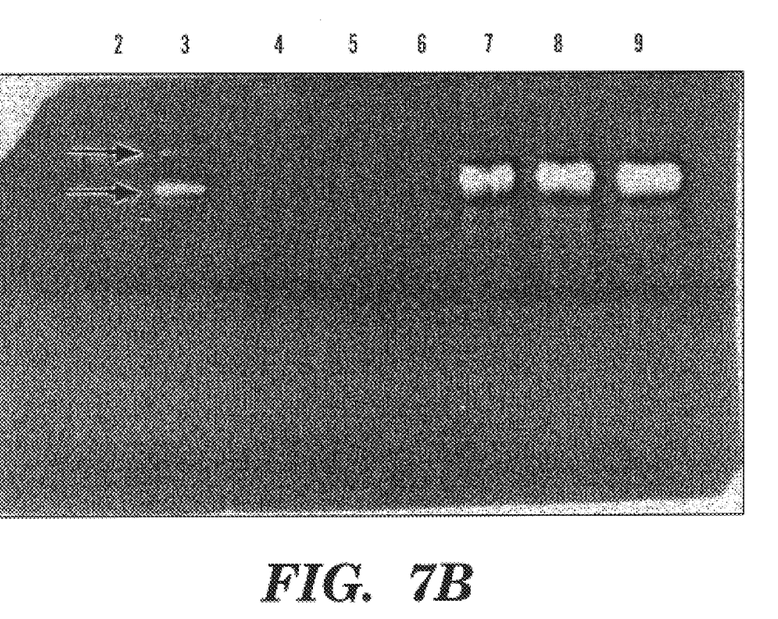
Figure 8:
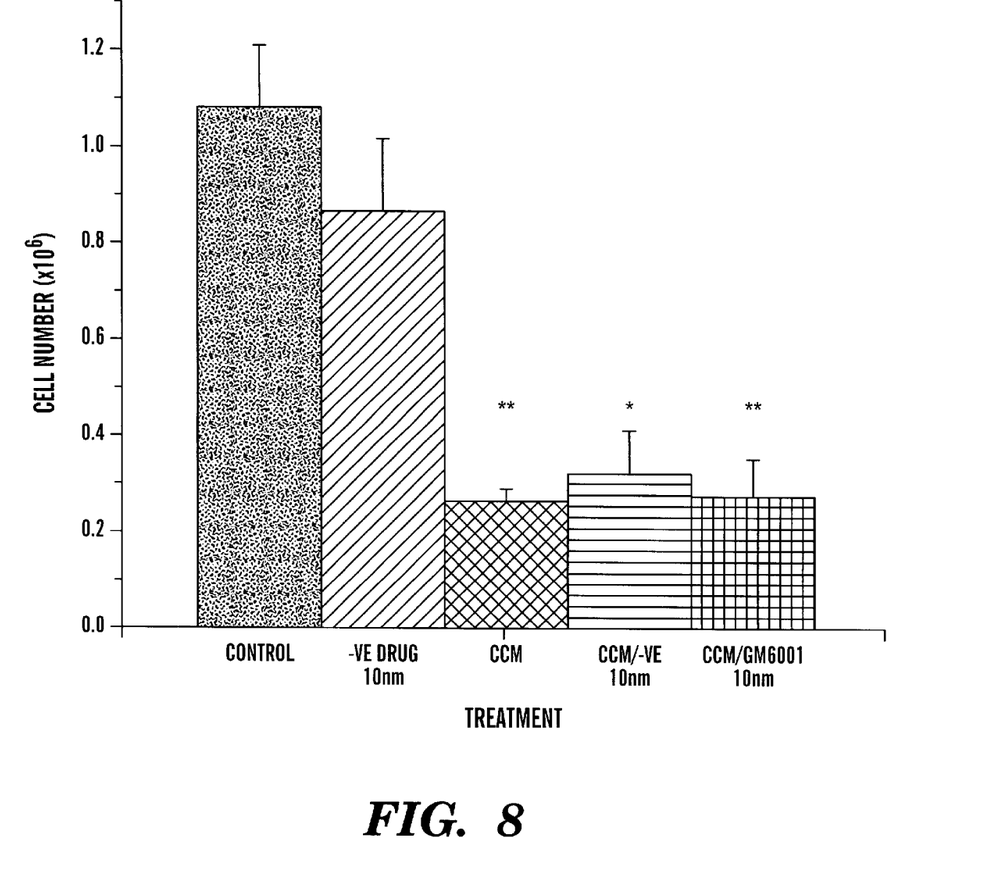
FIG. 8 is a graph illustrating the influence of MMP inhibitor on REC proliferation in the presence of CCM with either 10 nM GM600 1, the MMP inhibitor, or control drug; similar results were obtained using 50 nM. Values represent mean cell number±SEM from triplicate dishes in a representative experiment. Viability ranged from 91–89% and were not significantly different among the treatment groups; *indicates a significant difference between control and treated groups with p<0.01 and**indicates a significant difference with p<0.001.

In order to investigate whether MMPs were directly responsible for diminished REC proliferation, an inhibitor of matrix metalloproteinases (GM6001) or its control peptide were added to REC cultured with or without CCM and cell number was determined after 7 days in culture. Addition of GM6001 or its control peptide at a concentration of 5 nM (10 fold higher than the Kj) did not block marker protein activity in pooled CCM as determined by gelatin zymography (FIGS. 7A–B), nor was proliferation positively affected by addition of the inhibitor. In a second series of experiments, GM6001 or control peptide were used at concentrations of 10 and 50 W, but once again proliferation was not restored to control levels (FIG. 8).

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A composite cell culture comprising:
   a first layer comprising chondrocytes in an extracellular matrix;
   a second layer, disposed on the first layer, comprising type I collagen; and
   a third layer, disposed on the second layer, comprising cells other than chondrocytes at least partially covering the second layer.

2. The composite cell culture according to claim 1, wherein the cells are epithelial cells, fibroblasts, endothelial cells, epidermal cells, muscle cells, or combinations thereof.

3. The composite cell culture according to claim 2, wherein the cells are epithelial cells.

4. The composite cell culture according to claim 3, wherein the epithelial cells are upper respiratory epithelial cells.

5. The composite cell culture according to claim 3, wherein the epithelial cells are present as a plurality of distinct plaques dispersed throughout the third layer.

6. The composite cell culture according to claim 5, wherein the extracellular matrix is type II collagen.

7. The composite cell culture according to claim 1, wherein the chondrocytes are articular or upper airway cartilage chondrocytes.

8. The composite cell culture according to claim 7, wherein the cells are upper respiratory epithelial cells.

9. The composite cell culture according to claim 8, wherein the upper respiratory epithelial cells are present as a plurality of distinct plaques dispersed throughout the third layer.

10. The composite cell culture according to claim 7, wherein the extracellular matrix is type II collagen.

11. The composite cell culture according to claim 7, wherein chondrocytes are upper airway cartilage chondrocytes.

* * * * *